(12) United States Patent
Bilsky et al.

(10) Patent No.: US 9,234,023 B2
(45) Date of Patent: Jan. 12, 2016

(54) GLUCAGON-LIKE PEPTIDE-1 GLYCOPEPTIDES

(75) Inventors: Edward J. Bilsky, Biddeford, ME (US); Robin Polt, Tucson, AZ (US); Hanoch Senderowitz, Tel Aviv (IL)

(73) Assignee: Biousian Biosystems, Inc., Lexington, MA (US)

( * ) Notice: Subject to any disclaimer, the term of this patent is extended or adjusted under 35 U.S.C. 154(b) by 0 days.

(21) Appl. No.: 13/805,461

(22) PCT Filed: Jun. 24, 2011

(86) PCT No.: PCT/US2011/001141
§ 371 (c)(1),
(2), (4) Date: Jul. 8, 2013

(87) PCT Pub. No.: WO2011/162830
PCT Pub. Date: Dec. 29, 2011

(65) Prior Publication Data
US 2013/0281368 A1  Oct. 24, 2013

Related U.S. Application Data

(60) Provisional application No. 61/398,347, filed on Jun. 24, 2010.

(51) Int. Cl.
*A61K 38/22* (2006.01)
*C07K 14/575* (2006.01)
*C07K 14/605* (2006.01)
*A61K 47/48* (2006.01)
*A61K 38/00* (2006.01)

(52) U.S. Cl.
CPC .............. *C07K 14/605* (2013.01); *A61K 38/22* (2013.01); *A61K 47/48092* (2013.01); *C07K 14/575* (2013.01); *A61K 38/00* (2013.01)

(58) Field of Classification Search
None
See application file for complete search history.

(56) References Cited

U.S. PATENT DOCUMENTS

| 2004/0053370 | A1 * | 3/2004 | Glaesner et al. ............. 435/69.7 |
| 2004/0116339 | A1 * | 6/2004 | Villanueva et al. ............. 514/12 |
| 2008/0300173 | A1 * | 12/2008 | DeFrees .......................... 514/8 |
| 2009/0111739 | A1 * | 4/2009 | Kajihara et al. .................. 514/8 |
| 2010/0016547 | A1 * | 1/2010 | Ito et al. ......................... 530/324 |
| 2011/0195897 | A1 * | 8/2011 | Kajihara et al. ............... 514/7.2 |

FOREIGN PATENT DOCUMENTS

WO    WO 2007063907 A1 *  6/2007

OTHER PUBLICATIONS

Kong et al. Long-acting hyaluronate-exendin 4 conjugate for the treatment of type 2 diabetes. Biomaterials. Feb. 10, 2010, vol. 31, pp. 4121-4128.*
Ueda et al. Identification of glycosylated exendin-4 analogue with prolonged blood glucose-lowering activity through glycosylation scanning substitution. Bioorganic & Medicinal Chemistry Letters. Jun. 4, 2010, vol. 20, pp. 4631-4634.*
Siegel et al. Biological activity of GLP-1-analogues with N-terminal modifications. Regulatory Peptides. 1999, vol. 79, pp. 93-102.*
Deacon, "Therapeutic Strategies Based on Glucagon-Like Peptide 1," Diabetes, 53:2181-2189, Sep. 2004.
Green et al., "Metabolic Stability, Receptor Binding, cAMP Generation, Insulin Secretion and Antihyperglycaemic Activity of Novel N-Terminal Glu9-Substituted Analogues of Glucagon-Like Peptide-1," Biol. Chem., 384:1543-1551, Dec. 2003.
Meier et al., "Glucagon-like peptide 1(GLP-1) in biology and pathology," Diabetes Metab Res Rev 21:91-117, 2005.
Nauck et al., "Glucagon-like peptide 1 and its derivatives in the treatment of diabetes," Regulatory Peptides, 128:135-148, 2005.
Ueda et al., "Chemoenzymatic Synthesis of Glycosylated Glucagon-like Peptide 1: Effect of Glcosylation on Proteolytic Resistance and in Vivo Blood Glucose-Lowering Activity," J. Am. Chem. Soc. 131:6237-6245, 2009.

* cited by examiner

*Primary Examiner* — Jeffrey E Russel
(74) *Attorney, Agent, or Firm* — Steven R. Lazar

(57) ABSTRACT

Methods and materials are provided for the production of glycosylated GLP-1 peptides that exhibit improved properties. The methods and materials of the present invention may be used for treatment of metabolic conditions, such as Syndrome X and diabetes.

2 Claims, No Drawings

SEQUENCE LISTING

```
<160> NUMBER OF SEQ ID NOS: 33

<210> SEQ ID NO 1
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Gly, Ser or Ala
<220> FEATURE:
<221> NAME/KEY: MOD_RES
<222> LOCATION: (3)..(3)
<223> OTHER INFORMATION: Glu or Ala
<220> FEATURE:
<221> NAME/KEY: MOD_RES
<222> LOCATION: (5)..(5)
<223> OTHER INFORMATION: Thr or Ala
<220> FEATURE:
<221> NAME/KEY: MOD_RES
<222> LOCATION: (8)..(8)
<223> OTHER INFORMATION: Ser or Ala
<220> FEATURE:
<221> NAME/KEY: MOD_RES
<222> LOCATION: (8)..(8)
<223> OTHER INFORMATION: May or may not be glycosylated
<220> FEATURE:
<221> NAME/KEY: MOD_RES
<222> LOCATION: (10)..(10)
<223> OTHER INFORMATION: Val, Leu or Ala
<220> FEATURE:
<221> NAME/KEY: MOD_RES
<222> LOCATION: (11)..(11)
<223> OTHER INFORMATION: Ser or Ala
<220> FEATURE:
<221> NAME/KEY: MOD_RES
<222> LOCATION: (12)..(12)
<223> OTHER INFORMATION: Ser, Lys or Ala
<220> FEATURE:
<221> NAME/KEY: MOD_RES
<222> LOCATION: (13)..(13)
<223> OTHER INFORMATION: Tyr or Gln
<220> FEATURE:
<221> NAME/KEY: MOD_RES
<222> LOCATION: (14)..(14)
<223> OTHER INFORMATION: Leu, Met or Ala
<220> FEATURE:
<221> NAME/KEY: MOD_RES
<222> LOCATION: (14)..(14)
<223> OTHER INFORMATION: May or may not be glycosylated
<220> FEATURE:
<221> NAME/KEY: MOD_RES
<222> LOCATION: (16)..(16)
<223> OTHER INFORMATION: Gly, Glu or Ala
<220> FEATURE:
<221> NAME/KEY: MOD_RES
<222> LOCATION: (17)..(17)
```

```
<223> OTHER INFORMATION: Gln, Glu or Ala
<220> FEATURE:
<221> NAME/KEY: MOD_RES
<222> LOCATION: (17)..(17)
<223> OTHER INFORMATION: May or may not be glycosylated
<220> FEATURE:
<221> NAME/KEY: MOD_RES
<222> LOCATION: (19)..(19)
<223> OTHER INFORMATION: Ala or Val
<220> FEATURE:
<221> NAME/KEY: MOD_RES
<222> LOCATION: (20)..(20)
<223> OTHER INFORMATION: Lys or Arg
<220> FEATURE:
<221> NAME/KEY: MOD_RES
<222> LOCATION: (21)..(21)
<223> OTHER INFORMATION: Glu, Leu or Ala
<220> FEATURE:
<221> NAME/KEY: MOD_RES
<222> LOCATION: (24)..(24)
<223> OTHER INFORMATION: Ala, Glu or Gln
<220> FEATURE:
<221> NAME/KEY: MOD_RES
<222> LOCATION: (24)..(24)
<223> OTHER INFORMATION: May or may not be glycosylated
<220> FEATURE:
<221> NAME/KEY: MOD_RES
<222> LOCATION: (26)..(26)
<223> OTHER INFORMATION: Leu or Ala
<220> FEATURE:
<221> NAME/KEY: MOD_RES
<222> LOCATION: (27)..(27)
<223> OTHER INFORMATION: Val, Lys or Ala
<220> FEATURE:
<221> NAME/KEY: MOD_RES
<222> LOCATION: (28)..(28)
<223> OTHER INFORMATION: Lys, Asn, Glu, Arg or Ala
<220> FEATURE:
<221> NAME/KEY: MOD_RES
<222> LOCATION: (28)..(28)
<223> OTHER INFORMATION: May or may not be glycosylated
<220> FEATURE:
<221> NAME/KEY: MOD_RES
<222> LOCATION: (29)..(29)
<223> OTHER INFORMATION: Gly or Ala
<220> FEATURE:
<221> NAME/KEY: MOD_RES
<222> LOCATION: (30)..(30)
<223> OTHER INFORMATION: Arg, Gly or Ala
<220> FEATURE:
<221> NAME/KEY: MOD_RES
<222> LOCATION: (30)..(30)
<223> OTHER INFORMATION: May or may not be glycosylated
<220> FEATURE:
<223> OTHER INFORMATION: C-term may be NH2 or OH
<220> FEATURE:
<223> OTHER INFORMATION: see specification as filed for detailed
      description of substitutions and preferred embodiments

<400> SEQUENCE: 1

His Xaa Xaa Gly Xaa Phe Thr Xaa Asp Xaa Xaa Xaa Xaa Xaa Glu Xaa
1               5                   10                  15

Xaa Ala Xaa Xaa Xaa Phe Ile Xaa Trp Xaa Xaa Xaa Xaa Xaa
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Ser or Ala
```

```
<220> FEATURE:
<221> NAME/KEY: MOD_RES
<222> LOCATION: (8)..(8)
<223> OTHER INFORMATION: May or may not be glycosylated
<220> FEATURE:
<221> NAME/KEY: MOD_RES
<222> LOCATION: (14)..(14)
<223> OTHER INFORMATION: Leu, Met or Ala
<220> FEATURE:
<221> NAME/KEY: MOD_RES
<222> LOCATION: (14)..(14)
<223> OTHER INFORMATION: May or may not be glycosylated
<220> FEATURE:
<221> NAME/KEY: MOD_RES
<222> LOCATION: (17)..(17)
<223> OTHER INFORMATION: Gln, Glu or Ala
<220> FEATURE:
<221> NAME/KEY: MOD_RES
<222> LOCATION: (17)..(17)
<223> OTHER INFORMATION: May or may not be glycosylated
<220> FEATURE:
<221> NAME/KEY: MOD_RES
<222> LOCATION: (24)..(24)
<223> OTHER INFORMATION: Ala, Glu or Gln
<220> FEATURE:
<221> NAME/KEY: MOD_RES
<222> LOCATION: (24)..(24)
<223> OTHER INFORMATION: May or may not be glycosylated
<220> FEATURE:
<221> NAME/KEY: MOD_RES
<222> LOCATION: (28)..(28)
<223> OTHER INFORMATION: Lys, Asn, Glu, Arg or Ala
<220> FEATURE:
<221> NAME/KEY: MOD_RES
<222> LOCATION: (28)..(28)
<223> OTHER INFORMATION: May or may not be glycosylated
<220> FEATURE:
<221> NAME/KEY: MOD_RES
<222> LOCATION: (30)..(30)
<223> OTHER INFORMATION: Arg, Gly or Ala
<220> FEATURE:
<221> NAME/KEY: MOD_RES
<222> LOCATION: (30)..(30)
<223> OTHER INFORMATION: May or may not be glycosylated
<220> FEATURE:
<223> OTHER INFORMATION: C-term may be NH2 or OH
<220> FEATURE:
<223> OTHER INFORMATION: see specification as filed for detailed
      description of substitutions and preferred embodiments

<400> SEQUENCE: 2

His Ala Glu Gly Thr Phe Thr Xaa Asp Val Ser Ser Tyr Xaa Glu Gly
1               5                   10                  15

Xaa Ala Ala Lys Glu Phe Ile Xaa Trp Leu Val Xaa Gly Xaa
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: May or may not be glycosylated
<220> FEATURE:
<221> NAME/KEY: MOD_RES
<222> LOCATION: (14)..(14)
<223> OTHER INFORMATION: May or may not be glycosylated
<220> FEATURE:
<221> NAME/KEY: MOD_RES
<222> LOCATION: (17)..(17)
<223> OTHER INFORMATION: May or may not be glycosylated
<220> FEATURE:
```

```
<221> NAME/KEY: MOD_RES
<222> LOCATION: (24)..(24)
<223> OTHER INFORMATION: May or may not be glycosylated
<220> FEATURE:
<221> NAME/KEY: MOD_RES
<222> LOCATION: (28)..(28)
<223> OTHER INFORMATION: May or may not be glycosylated
<220> FEATURE:
<221> NAME/KEY: MOD_RES
<222> LOCATION: (30)..(30)
<223> OTHER INFORMATION: May or may not be glycosylated
<220> FEATURE:
<223> OTHER INFORMATION: C-term may be NH2 or OH
<220> FEATURE:
<223> OTHER INFORMATION: see specification as filed for detailed
      description of substitutions and preferred embodiments

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Glycosylated residue
<220> FEATURE:
<223> OTHER INFORMATION: C-term NH2

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Glycosylated residue
<220> FEATURE:
<223> OTHER INFORMATION: C-term NH2

<400> SEQUENCE: 5

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (30)..(30)
<223> OTHER INFORMATION: Glycosylated residue
<220> FEATURE:
<223> OTHER INFORMATION: C-term NH2

<400> SEQUENCE: 6

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Glycosylated residue
<220> FEATURE:
<223> OTHER INFORMATION: C-term NH2

<400> SEQUENCE: 7

His Ala Glu Gly Thr Phe Thr Ala Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Glycosylated residue
<220> FEATURE:
<223> OTHER INFORMATION: C-term NH2

<400> SEQUENCE: 8

His Ala Glu Gly Thr Phe Thr Ser Asp Val Ser Ser Tyr Ala Glu Gly
 1               5                  10                  15

Gln Ala Ala Lys Glu Phe Ile Ala Trp Leu Val Lys Gly Arg
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Glycosylated residue
<220> FEATURE:
<223> OTHER INFORMATION: C-term NH2

<400> SEQUENCE: 9

His Ala Glu Gly Thr Phe Thr Ser Asp Val Ser Ser Tyr Leu Glu Gly
```

```
1               5                   10                  15
Ala Ala Ala Lys Glu Phe Ile Ala Trp Leu Val Lys Gly Arg
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Glycosylated residue
<220> FEATURE:
<223> OTHER INFORMATION: C-term NH2

<400> SEQUENCE: 10

His Ala Glu Gly Thr Phe Thr Ser Asp Val Ser Ser Tyr Leu Glu Gly
1               5                   10                  15
Gln Ala Ala Lys Glu Phe Ile Ala Trp Leu Val Ala Gly Arg
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Glycosylated residue
<220> FEATURE:
<223> OTHER INFORMATION: C-term NH2

<400> SEQUENCE: 11

His Ala Glu Gly Thr Phe Thr Ser Asp Val Ser Ser Tyr Leu Glu Gly
1               5                   10                  15
Gln Ala Ala Lys Glu Phe Ile Ala Trp Leu Val Lys Gly Ala
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Glycosylated residue
<220> FEATURE:
<223> OTHER INFORMATION: C-term NH2

<400> SEQUENCE: 12

His Ala Glu Gly Thr Phe Thr Ala Asp Val Ser Ser Tyr Ala Glu Gly
1               5                   10                  15
Gln Ala Ala Lys Glu Phe Ile Ala Trp Leu Val Lys Gly Arg
            20                  25                  30

<210> SEQ ID NO 13
<211> LENGTH: 30
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Glycosylated residue
<220> FEATURE:
<223> OTHER INFORMATION: C-term NH2

<400> SEQUENCE: 13

His Ala Glu Gly Thr Phe Thr Ser Asp Val Ser Ser Tyr Ala Glu Gly
1               5                   10                  15

Ala Ala Ala Lys Glu Phe Ile Ala Trp Leu Val Lys Gly Arg
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Glycosylated residue
<220> FEATURE:
<223> OTHER INFORMATION: C-term NH2

<400> SEQUENCE: 14

His Ala Glu Gly Thr Phe Thr Ser Asp Val Ser Ser Tyr Leu Glu Gly
1               5                   10                  15

Ala Ala Ala Lys Glu Phe Ile Ala Trp Leu Val Lys Gly Arg
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Glycosylated residue
<220> FEATURE:
<223> OTHER INFORMATION: C-term NH2

<400> SEQUENCE: 15

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Ala Gly Ala
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Glycosylated residue
<220> FEATURE:
<223> OTHER INFORMATION: C-term NH2
```

```
<400> SEQUENCE: 16

His Ala Glu Gly Thr Phe Thr Ala Asp Val Ser Ser Tyr Leu Glu Gly
1               5                   10                  15

Gln Ala Ala Lys Glu Phe Ile Ala Trp Leu Val Lys Gly Ala
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Glycosylated residue
<220> FEATURE:
<223> OTHER INFORMATION: C-term NH2

<400> SEQUENCE: 17

His Ala Glu Gly Thr Phe Thr Ser Asp Val Ser Ser Tyr Ala Glu Gly
1               5                   10                  15

Gln Ala Ala Lys Glu Phe Ile Ala Trp Leu Val Ala Gly Arg
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Glycosylated residue
<220> FEATURE:
<223> OTHER INFORMATION: C-term NH2

<400> SEQUENCE: 18

His Ala Glu Gly Thr Phe Thr Ala Asp Val Ser Ser Tyr Ala Glu Gly
1               5                   10                  15

Ala Ala Ala Lys Glu Phe Ile Ala Trp Leu Val Lys Gly Arg
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Glycosylated residue
<220> FEATURE:
<223> OTHER INFORMATION: C-term NH2

<400> SEQUENCE: 19

His Ala Glu Gly Thr Phe Thr Ser Asp Val Ser Ser Tyr Ala Glu Gly
1               5                   10                  15

Ala Ala Ala Lys Glu Phe Ile Ala Trp Leu Val Ala Gly Arg
            20                  25                  30

<210> SEQ ID NO 20
```

```
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Glycosylated residue
<220> FEATURE:
<223> OTHER INFORMATION: C-term NH2

<400> SEQUENCE: 20

His Ala Glu Gly Thr Phe Thr Ser Asp Val Ser Ser Tyr Leu Glu Gly
1               5                   10                  15

Ala Ala Ala Lys Glu Phe Ile Ala Trp Leu Val Ala Gly Ala
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Glycosylated residue
<220> FEATURE:
<223> OTHER INFORMATION: C-term NH2

<400> SEQUENCE: 21

His Ala Glu Gly Thr Phe Thr Ala Asp Val Ser Ser Tyr Leu Glu Gly
1               5                   10                  15

Ala Ala Ala Lys Glu Phe Ile Ala Trp Leu Val Ala Gly Arg
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Glycosylated residue
<220> FEATURE:
<223> OTHER INFORMATION: C-term NH2

<400> SEQUENCE: 22

His Ala Glu Gly Thr Phe Thr Ser Asp Val Ser Ser Tyr Ala Glu Gly
1               5                   10                  15

Gln Ala Ala Lys Glu Phe Ile Ala Trp Leu Val Ala Gly Ala
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Glycosylated residue
```

-continued

```
<220> FEATURE:
<223> OTHER INFORMATION: C-term NH2

<400> SEQUENCE: 23

His Ala Glu Gly Thr Phe Thr Ala Asp Val Ser Ser Tyr Leu Glu Gly
1               5                   10                  15

Gln Ala Ala Lys Glu Phe Ile Ala Trp Leu Val Ala Gly Ala
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Glycosylated residue
<220> FEATURE:
<223> OTHER INFORMATION: C-term NH2

<400> SEQUENCE: 24

His Ala Glu Gly Thr Phe Thr Ala Asp Val Ser Ser Tyr Ala Glu Gly
1               5                   10                  15

Ala Ala Ala Lys Glu Phe Ile Ala Trp Leu Val Ala Gly Arg
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Glycosylated residue
<220> FEATURE:
<223> OTHER INFORMATION: C-term NH2

<400> SEQUENCE: 25

His Ala Glu Gly Thr Phe Thr Ser Asp Val Ser Ser Tyr Ala Glu Gly
1               5                   10                  15

Ala Ala Ala Lys Glu Phe Ile Ala Trp Leu Val Ala Gly Ala
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Glycosylated residue
<220> FEATURE:
<223> OTHER INFORMATION: C-term NH2

<400> SEQUENCE: 26

His Ala Glu Gly Thr Phe Thr Ala Asp Val Ser Ser Tyr Ala Glu Gly
1               5                   10                  15

Gln Ala Ala Lys Glu Phe Ile Ala Trp Leu Val Ala Gly Ala
            20                  25                  30
```

```
<210> SEQ ID NO 27
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Glycosylated residue
<220> FEATURE:
<221> NAME/KEY: MOD_RES
<222> LOCATION: (17)..(17)
<223> OTHER INFORMATION: Glycosylated residue
<220> FEATURE:
<221> NAME/KEY: MOD_RES
<222> LOCATION: (30)..(30)
<223> OTHER INFORMATION: Glycosylated residue
<220> FEATURE:
<223> OTHER INFORMATION: C-term NH2

<400> SEQUENCE: 27

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-Ala

<400> SEQUENCE: 28

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 29
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Glycosylated residue

<400> SEQUENCE: 29

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 30
```

```
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (30)..(30)
<223> OTHER INFORMATION: Glycosylated residue

<400> SEQUENCE: 30

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Ser
            20                  25                  30

<210> SEQ ID NO 31
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (31)..(31)
<223> OTHER INFORMATION: Glycosylated residue

<400> SEQUENCE: 31

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Ser
            20                  25                  30

<210> SEQ ID NO 32
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (29)..(29)
<223> OTHER INFORMATION: Aib
<220> FEATURE:
<221> NAME/KEY: MOD_RES
<222> LOCATION: (31)..(31)
<223> OTHER INFORMATION: Glycosylated residue

<400> SEQUENCE: 32

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Xaa Arg Ser
            20                  25                  30

<210> SEQ ID NO 33
```

```
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

GLUCAGON-LIKE PEPTIDE-1 GLYCOPEPTIDES

CROSS-REFERENCE TO RELATED APPLICATIONS

This is the U.S. national phase of International Patent Application No. PCT/US11/01141, filed Jun. 24, 2011, which claims priority to and the benefit of U.S. Provisional Patent Application No. 61/398,347, filed on Jun. 24, 2010, the contents of which are incorporated by reference herein.

REFERENCE TO SEQUENCE LISTING

This application includes as part of the originally filed subject matter a Sequence Listing electronically submitted via EFS-Web on Dec. 19, 2012, as a single text file named "SEQUENCE_LISTING_ST25.txt". The Sequence Listing text file was created on Dec. 19, 2012 and is 14 kb in size. The contents of the Sequence Listing are hereby incorporated by reference.

FIELD OF THE INVENTION

The present invention relates to glycosylated peptides with high affinity for glucagon-like peptide-1 receptors. The peptides, and compositions comprising them, are useful for treatment of metabolic disorders, including syndrome X (consisting of such abnormalities as obesity, dyslipidemia, hypercoagulation, hypertension, insulin resistance leading to heart disease and diabetes), obesity, diabetes, neurodegenerative disease, immunological disease, bleeding disorders, and/or cancer. More specifically, it relates to such compounds that are capable of inhibiting DPP-IV which is a negative regulator of proglucagon and improves insulin-sensitivity.

BACKGROUND OF THE INVENTION

Glucagon-like peptide-1 (GLP-1), also known as proglucagon, induces numerous biological effects such as stimulating insulin secretion, inhibiting glucagon secretion, inhibiting gastric emptying, inhibiting gastric motility or intestinal motility, enhancing glucose utilization, and inducing weight loss. GLP-1 may further act to prevent the deterioration of pancreatic beta-cells that occurs as non-insulin dependent diabetes mellitus progresses. A significant characteristic of GLP-1 is its ability to stimulate insulin secretion without the associated risk of hypoglycemia that is seen when using insulin therapy or some types of oral therapies that act by increasing insulin expression.

The usefulness of therapy involving GLP-1 peptides has been limited by the fact that GLP-1(1-37) is poorly active, and the two naturally occurring truncated peptides, GLP-1(7-37)OH and GLP-1(7-36)NH$_2$, have extremely short in vivo half lives and are rapidly inactivated and cleared. Endogenously produced dipeptidyl-peptidase IV (DPP-IV) inactivates circulating GLP-1 peptides by removing the N-terminal histidine and alanine residues and is a major reason for the short in vivo half-life.

Various approaches have been undertaken to extend the half-life of GLP-1 peptides or reduce clearance of the peptides from the body while maintaining biological activity. U.S. Pat. No. 5,705,483 teaches GLP-1 peptide analogs made resistant to DPP-IV degradation by the incorporation of modifications at the N-terminus of the peptide. An alternative approach for extending the half-life of GLP-1 peptides is derivatization, wherein large acyl groups that prevent DPP-IV from accessing the N-terminus of the peptide are attached to various amino acids of GLP-1 (See International Application No. PCT/DK97/00340, filed Aug. 22, 1997 entitled "GLP-1 Derivatives," which claims the benefit of DK Provisional Application Nos. 0931/96 filed Aug. 30, 1996, 1259/96 filed Nov. 8, 1996 and 1470/96 filed Dec. 20, 1996). A third approach for extending the half-life of GLP-1 peptides is the covalent attachment of one or more molecules of polyethylene glycol (PEG) to particular residues of a GLP-1 compound to produce a biologically active, PEGylated GLP-1 (See U.S. Pat. No. 7,557,183).

Other therapeutic strategies based on GLP-1 have included the development of enzyme-resistant GLP-1 analogs, such as Exendin-4, a GLP-1 receptor agonist originally isolated from the venom of the Gila monster, with significant homology to native GLP-1. Exendin-4 is resistant to the activity of DPP-IV because of a penultimate glycine residue in place of alanine, and survives longer in circulation. Additionally, small molecule inhibitors, such as DPP-IV inhibitors, have been studied for their ability to extend the metabolic stability and improve the antihyperglycemic and insulinotropic effects of exogenous GLP-1. See, Deacon, Diabetes 53:2181-89 (2004).

In addition to the above, recent attempts have been made to improve the proteolytic resistance and in vivo activity of GLP-1 by preparing variants of GLP-1 such as amino acid substitution and/or synthesis of glycosylated GLP-1 peptides. See Green et al., Biol. Chem., 384:1543-51 (2003); Ueda et al., J. Am. Chem. Soc. 131:6237-45 (2009) prepared glycosylated GLP-1 glycopeptides having one to three glycan groups [GlcNAc, LacNAc and Sialyl LacNAc] added at amino acid residues 19, 26, 34 and 37. However, there remains a critical need for improved GLP-1 peptides with improved metabolic stability and efficacy.

BRIEF SUMMARY OF THE INVENTION

The present invention provides novel GLP-1 glycopeptides with improved metabolic stability. The invention also provides methods for delivering therapy for conditions such as metabolic disorders such as Syndrome X and Type II diabetes, by administering to an individual an effective amount of a glycosylated GLP-1 peptide. The glycosylated GLP-1 peptides of the present invention are typically between twenty eight and 32 amino acids in length, may contain amino acid substitutions at up to about eighteen residues of GLP-1, and may be glycosylated at from one to about six peptide residues. In certain embodiments, the peptide is glycosylated with a sugar moiety selected from a monosaccharide, disaccharide or trisaccharide sugar moiety.

In other embodiments, the glycosylated peptides of the present invention are formulated into compositions, which compositions may be used for the treatment of metabolic conditions, including conditions that involve glucagon secretion, gastric emptying and excess appetite. Additionally, the compositions of the present invention may be used for treatment of conditions such as Syndrome X and Type II diabetes. The compositions may include one or more additional active agents, such as anti-inflammatory agents or anti-pain agents, as well as one or more inactive agents, which may include carriers, delivery vehicles, binding agents, diluents, disintegrants, lubricants, buffers, and other pharmaceutically acceptable excipients.

In certain embodiments, the present invention includes glycosylated peptides comprising the following amino acid sequence [using standard single letter codes, and x# and y# denoting variable residues; and a/b meaning the residue may be either a or b]:

[SEQ ID NO: 1]
```
H x2 x3 G x5 F T y8 D x10 x11 x12 x13 y14

E x16 y17 A x19 x20 x21 F I y24 W x26 x27 y28 x29 y30 - B
``` wherein: B is selected from NH2 and OH; x2=G/S/A; x3=E/A; x5=T/A; Y8=S/A; x10=V/L/A; x11=S/A; x12=S/K/A; x13=Y/Q; Y14=L/M/A; x16=G/E/A; y17=Q/E/A; x19=A/V; x20=K/R; X21=E/L/A; y24=A/E/Q; x26=L/A; x27=V/K/A; y28=K/N/E/R/A; X29=G,A; y30=R/G/A;

and wherein at least one of y8, y14, y17, y24, y28 and y30 is glycosylated. In preferred embodiments, at least one of y17, y24 and y30 is glycosylated with a sugar residue selected from the group consisting of glucose (Glc); galactose; xylose; fructose; mannose; fucose; ribose; deoxyribose; arabinose; rhamnose; sucrose; trehalose; saccharose; maltose; and lactose.

In other preferred embodiments, the glycosylated peptide of the present invention comprises the amino acid sequence of SEQUENCE ID NO. 1, above, wherein at least one of y8, y14, y17, y24, y28 and y30 is glycosylated; and at least one of y8, y14, y17, y24, y28 and y30 is alanine. In preferred embodiments, the glycosylated peptide of the present invention comprises the amino acid sequence of SEQUENCE ID NO. 1, wherein each of y8, y14, y17, y24, y28 and y30 is either a glycosylated amino acid or alanine.

In additional embodiments, the glycosylated peptide of the present invention comprises the following sequence:

[SEQ ID NO: 2]
```
H A E G T F T y8 D V S S Y y14 E G y17 A

A K E F I y24 W L V y28 G y30 - B
```

Wherein B is selected from NH2 and OH; y8=S/A; y14=L/M/A; y17=Q/E/A; Y24=A/E/Q; y28=K/N/E/R/A; y30=R/G/A;

and wherein at least one of y8, y14, y17, y24, y28 and y30 is glycosylated. In preferred embodiments, at least one of y17, y24 and y30 is glycosylated with a sugar residue selected from the group consisting of glucose (Glc); galactose; xylose; fructose; mannose; fucose; ribose; deoxyribose; arabinose; rhamnose; sucrose; trehalose; saccharose; maltose; and lactose.

In other preferred embodiments, the glycosylated peptide of the present invention comprises the amino acid sequence of SEQUENCE ID NO. 2, above, wherein at least one of y8, y14, y17, y24, y28 and y30 is glycosylated; and at least one of y8, y14, y17, y24, y28 and y30 is alanine. In preferred embodiments, the glycosylated peptide of the present invention comprises the amino acid sequence of SEQUENCE ID NO. 2, wherein each of y8, y14, y17, y24, y28 and y30 is either a glycosylated amino acid or alanine.

In other embodiments, the glycosylated peptide of the present invention comprises the following amino acid sequence:

[SEQ ID NO: 3]
```
H A E G T F T S* D V S S Y L* E G Q* A

A K E F I A* W L V K* G R* - B
``` wherein: B is selected from NH2 and OH; and wherein at least one of the asterisked amino acids is glycosylated. In preferred embodiments, at least one of one of the asterisked amino acids is glycosylated with a sugar residue selected from the group consisting of glucose; galactose; xylose; fructose; mannose; fucose; ribose; deoxyribose; arabinose; rhamnose; sucrose; trehalose; saccharose; maltose; and lactose.

In other preferred embodiments, the glycosylated peptide of the present invention comprises the amino acid sequence of SEQUENCE ID NO. 3, above, wherein at least one of the asterisked amino acids is glycosylated; and at least one of the asterisked amino acids is alanine. In preferred embodiments, the glycosylated peptide of the present invention comprises the amino acid sequence of SEQUENCE ID NO. 3, wherein each of the asterisked amino acids is either a glycosylated amino acid or alanine.

In certain embodiments, the glycosylated peptide of the present invention comprises one or more glycosylated residues, preferably from 1 to 6 amino acids to which a glycan moiety has been attached. The glycan moiety is preferably a saccharide, including mono-, di- and trisaccharides. In other embodiments, the glycan moiety may be an oligosaccharide [with four or more linked saccharide] or a polysaccharide. Other molecules, such as glycosaminoglycans may also be used as one or more glycan moiety attached to the peptide chains. The glycans may be attached to the peptide through any known means, whether enzymatic or synthetic, including means described in U.S. Pat. Nos. 5,470,949 and 5,767,254, the disclosure of which are hereby incorporated by reference.

In preferred embodiments, at least one of y8, y14, y17, y24, y28 and y30 is glycosylated with a sugar residue selected from the group consisting of glucose (Glc); galactose; xylose; fructose; mannose; fucose; ribose; deoxyribose; arabinose; rhamnose; sucrose; trehalose; saccharose; maltose; and lactose.

Other object advantages and features of the present invention will be apparent from the following specification.

DETAILED DESCRIPTION OF THE INVENTION

The present invention provides novel GLP-1 compounds, as well as methods for their preparation, screening and use for the treatment of various physical and physiological ailments. The novel glycopeptides comprise a basic GLP-1 scaffold, with variations in certain amino acid residues, as well as variations of saccharide moieties attached at certain amino acid residues.

Glycopeptides are synthesized and screened for in vitro binding, selectivity and activity at GLP-1 receptors, as well as stability against DPP IV. These compounds will be tested upon multiple models of analgesia, including the treatment of chronic inflammatory pain.

The ability to synthesize glycosylated peptides is utilized in part to develop GLP-1 based peptides and to develop novel, safe and efficacious targeted delivery of compounds for the treatment of metabolic disorders, such as Syndrome X and diabetes. Glycosylation of the GLP-1 scaffold will enhance the resistance of the peptides to proteolytic enzymes and will enhance the GLP-1 activity.

This invention further comprises methods for synthesizing a library of GLP-1-based glycopeptides and obtain dosing and efficacy data in preclinical rodent models of diabetes and glycose metabolism.

It is expected that the effective doses will undergo reduced levels of proteolytic digestion by DPP-IV and/or neutral endopeptidase (NEP24.11). In the unlikely event that intolerable side effects are present, then that information will be used to help guide further refinement of the synthesis of GLP-1-based glycopeptides, or alternatively, another incretin hormone based scaffold. In the event that minimal activity is observed in the assay, alternative assays will be employed to assess binding, potency, efficacy and stability against DPP IV. The milestone will consist of the identification of a compound with insulinotropic activity, increased serum half-life and no significant gross observable side effects.

Glycosylated GLP-1 peptides are assessed in a number of models, including: competitive binding assay [receptor binding]; cAMP production assay [agonistic activities]; insulin secretion; proteolytic stability against human plasma, DPP-IV and NEP 24.11; in vivo blood glucose-lowering activity in normal and obese diabetic db/db mice. See Ueda et al., J. Am. Chem. Soc. (2009) 131:6237-45; Meier and Nauck, Diabetes Metab. Res. Rev (2005) 21:91-117; Deacon, Diabetes (2004) 53:-2184-89; Nauck and Meier, Regulatory Peptides (2005) 128:135-48; Green et al., Biol. Chem. (2003) 3854:1543-51. The disclosures of these publications are hereby incorporated herein by reference for its relevant teachings.

The design of additional compounds includes testing compounds with sugar residues with increased lipophilicity or hydrophilicity, as well as other parameters, such as amphipathicity. Additional compounds according to the present invention include those in the Table below:

TABLE 1

SEQUENCE OF ADDITIONAL GLYCOPEPTIDES

| PEPTIDE | SEQUENCE |
|---|---|
| BBI-21001 | Native GLP-1 H A E G T F T S D V S S Y L E G Q A A K E F I A W L V K G R [non-glycosylated] (Control) SEQUENCE ID NO 33 |
| BBI-21002 | $H_2$N-H A E G T F T S* D V S S Y L E G Q A A K E F I A W L V K G R-amide SEQUENCE ID NO 4 |
| BBI-21003 | $H_2$N- H A E G T F T S D V S S Y L E G Q* A A K E F I A W L V K G R-amide SEQUENCE ID NO 5 |
| BBI-21004 | $H_2$N- H A E G T F T S D V S S Y L E G Q A A K E F I A W L V K G R*-amide SEQUENCE ID NO 6 |
| BBI-21005 | $H_2$N- H A E G T F T A D V S S Y L E G Q* A A K E F I A W L V K G R-amide SEQUENCE ID NO 7 |
| BBI-21006 | $H_2$N- H A E G T F T S* D V S S Y A E G Q A A K E F I A W L V K G R-amide SEQUENCE ID NO 8 |
| BBI-21007 | $H_2$N - H A E G T F T S D V S S Y L E G A A A K E F I A W L V K G R*-amide SEQUENCE ID NO 9 |
| BBI-21008 | $H_2$N- H A E G T F T S D V S S Y L E G Q* A A K E F I A W L V A G R-amide SEQUENCE ID NO 10 |
| BBI-21009 | $H_2$N- H A E G T F T S* D V S S Y L E G Q A A K E F I A W L V K G A-amide SEQUENCE ID NO 11 |
| BBI-21010 | $H_2$N- H A E G T F T A D V S S Y A E G Q* A A K E F I A W L V K G R-amide SEQUENCE ID NO 12 |
| BBI-21011 | $H_2$N- H A E G T F T S* D V S S Y A E G A A A K E F I A W L V K G R-amide SEQUENCE ID NO 13 |
| BBI-21012 | $H_2$N- H A E G T F T S D V S S Y L E G A A A K E F I A W L V K G R*-amide SEQUENCE ID NO 14 |
| BBI-21013 | $H_2$N- H A E G T F T S* D V S S Y L E G Q A A K E F I A W L V A G A-amide SEQUENCE ID NO: 15 |
| BBI-21014 | $H_2$N-H A E G T F T A D V S S Y L E G Q* A A K E F I A W L V K G A-amide SEQUENCE ID NO: 16 |
| BBI-21015 | $H_2$N-H A E G T F T S D V S S Y A E G Q A A K E F I A W L V A G R*-amide SEQUENCE ID NO: 17 |
| BBI-21016 | $H_2$N-H A E G T F T A D V S S Y A E G A A A K E F I A W L V K G R*-amide SEQUENCE ID NO: 18 |
| BBI-21017 | $H_2$N-H A E G T F T S* D V S S Y A E G A A A K E F I A W L V A G R-amide SEQUENCE ID NO: 19 |
| BBI-21018 | $H_2$N-H A E G T F T S* D V S S Y L E G A A A K E F I A W L V A G A-amide SEQUENCE ID NO: 20 |
| BBI-21019 | $H_2$N-H A E G T F T A D V S S Y L E G A A A K E F I A W L V A G R*-amide SEQUENCE ID NO: 21 |
| BBI-21020 | $H_2$N-H A E G T F T S* D V S S Y A E G Q A A K E F I A W L V A G A-amide SEQUENCE ID NO: 22 |

TABLE 1-continued

SEQUENCE OF ADDITIONAL GLYCOPEPTIDES

| PEPTIDE | SEQUENCE |
|---|---|
| BBI-21021 | H$_2$N-H A E G T F T A D V S S Y L E G Q* A A K E F I A W L V A G A-amide SEQUENCE ID NO: 23 |
| BBI-21022 | H$_2$N-H A E G T F T A D V S S Y A E G A A A K E F I A W L V A G R*-amide SEQUENCE ID NO: 24 |
| BBI-21023 | H$_2$N-H A E G T F T S* D V S S Y A E G A A A K E F I A W L V A G A-amide SEQUENCE ID NO: 25 |
| BBI-21024 | H$_2$N-H A E G T F T A D V S S Y A E G Q* A A K E F I A W L V A G A -amide SEQUENCE ID NO: 26 |
| BBI-21025 | H$_2$N-H A E G T F T S* D V S S Y L E G Q* A A K E F I A W L V K G R* -amide SEQUENCE ID NO: 27 |
| BBI-22001 | H a E G T F T S D V S S Y L E G Q A A K E F I A W L V K G R SEQUENCE ID NO 28 |
| BBI-22002 | H G E G T F T S D L S K Q M E E E A V R L F I E W L K N G G P S S G A P P P S* SEQUENCE ID NO 29 |
| BBI-22003 | H a E G T F T S D V S S Y L E G Q A A K E F I A W L V K G S* SEQUENCE ID NO 30 |
| BBI-22004 | H a E G T F T S D V S S Y L E G Q A A K E F I A W L V K G R S* SEQUENCE ID NO 31 |
| BBI-22005 | H Aib E G T F T S D V S S Y L E G Q A A K E F I A W L V K Aib R S* SEQUENCE ID NO 32 |

* = glycosylated residue: (beta-D-Rhamnoside)-amide; (beta-Lactoside)-amide; (beta-D-Glc)-amide Amino Acids. In addition to the above peptides, the present invention also includes peptides wherein one or more of the amino acids listed in Tables 1 through 5 is replaced by the corresponding D-enantiomer, or by a non-naturally occurring amino acid analog.

Note that the following common abbreviations are used for amino acids: Alanine=A or Ala; Arginine=Arg or R; Asparagine=N or Asn; Aspartic Acid=Asp or D; Cysteine=C or Cys; Glutamic Acid=Glu or E; Glutamine=Gln or Q; Glycine=Gly or G; Histidine=His or H; Isoleucine=Ile or I; Leucine=Leu or L; Lysine=Lys or K; Methionine=Met or M; Phenylalanine=Phe or F; Proline=Pro or P; Serine=Ser or S; Threonine=Thr or T; Tryptophan Trp or W; Tyrosine=Tyr or Y; and Valine=Val or V. The D-enantiomer of an amino acid may be indicated by a small letter [e.g., 'a' for Alanine] or by the abbreviation "d" before the amino acid [e.g., dA or dAla].

Glycosylation. Suitable sugar or saccharide moieties for attachment to the glycopeptides of the present invention may include both natural and synthetically made saccharides. In preferred embodiments, the saccharides useful in the present invention may include monosaccharides, disaccharides, trisaccharides, oligosaccharides and polysaccharides, including but not limited to: the monosaccharides dihydroxyacetone, glyceraldehydes, aldotriose, erythrulose, erythrose, threose, ribulose, psicose, xylose, glucose (Glc), fructose, mannose, galactose, fucose, ribose, tagatose, arabinose, rhamnose, sedoheptalose and nonoses such as neuraminic acid, sialic acid; the disaccharides sucrose, trehalose, saccharose, maltose, lactose (Lac), turanose, cellobiose, gentibiose, isomaltose, melibiose, and primeveose; oligosaccharides such as maltotriose, raffinose, melicitose, acarbose, stachyose, and oligofructose. In certain embodiments, the saccharide moieties useful in the present invention may include polysaccharides, such as inulin, fructan, glycogen, amylose, pectin, amylopectin, dextrin/dextran, betaglucans, maltodextrin, mannans, chitins, inositols, such as myo-inositol, inositol phosphates and inositol hexanicotinate and glycosaminoglycans, such as heparin, heparin sulfate and chondroitin sulfate. It should be noted that, in order to accomplish glycosylation at a particular residue, that residue may need to be modified. For example, in order to attach a glycan via N-glycosylation at a site, it may be necessary to change the amino acid at that site to an asparagines (N, or Asn). In order to attach a glycan via O-glycosylation at a site, it may be necessary to change the amino acid at that cite to a threonine (T, or Thr) or a serine (S, or Ser). In general, O-glycosylation may be the preferred manner of attaching a glycan to a peptide.

Formulations. The compositions of the present invention may further comprise a pharmaceutically acceptable excipient, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars; starches; cellulose and its derivatives; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutically acceptable excipients which may be used in the manufacture of pharmaceutical compositions also include, but are not limited to, inert diluents, dispersing and/or granulating agents, surface active agents and/or emulsifiers, disintegrating agents, binding agents, preservatives (e.g., antioxidants, chelating agents, antimicrobial preservatives, antifungal preservatives, alcohol preservatives, acidic preservatives, and the like), buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

In certain embodiments, the composition further comprises one or more sugars. The term "sugar" as used herein refers to a natural or an unnatural monosaccharide, disaccharide, trisaccharide, oligosaccharide, or polysaccharide, comprising one or more triose, tetrose, pentose, hexose, heptose, octose, or nonose saccharides. Sugars may include substances derived from saccharides by reduction of the carbonyl group (alditols), by oxidation of one or more terminal groups to carboxylic acids (aldonic acids), or by replacement of one or more hydroxyl group(s) by a hydrogen (deoxy sugars), an amino group (amino sugars), a thiol group (thio sugars), an acylamino group, a sulfate group, a phosphate group, or similar heteroatomic group; or any combination of the foregoing modifications. The term sugar also includes derivatives of these compounds (i.e., sugars that have been chemically modified by acylation, alkylation, and formation of glycosidic bonds by reaction of sugar alcohols with aldehydes or ketones, etc). Sugars may be present in cyclic (oxiroses, oxetosesm furanoses, pyranoses, septanoses, octanoses, etc) form as hemiacetals, hemiketals, or lactones; or in acyclic form. The saccharides may be ketoses, aldoses, polyols and/or a mixture of ketoses, aldoses and polyols.

Exemplary sugars include, but are not limited to glycerol, polyvinylalcohol, propylene glycol, sorbitol, ribose, arabinose, xylose, lyxose, allose, altrose, mannose, mannitol, gulose, dextrose, idose, galactose, talose, glucose, fructose, dextrates, lactose, sucrose, starches (i.e., amylase and amylopectin), sodium starch glycolate, cellulose and cellulose derivatives (i.e., methylcellulose, hydroxypropyl cellulose, hydroxyethyl cellulose, hydroxyethylmethyl cellulose, carboxymethyl cellulose, cellulose acetate, cellulose acetate phthalate, croscarmellose, hypomellose, and hydroxypropyl methyl cellulose), carrageenan, cyclodextrins (e.g., hydroxypropyl-gamma-CD), dextrin, polydextrose, and trehalose.

In certain embodiments, the sugar is selected from lactose anhydrous, lactose monohydrate, trehalose and hydroxypropyl-gamma-CD.

In certain embodiments, the composition further comprises one or more polymers. In certain preferred embodiments, the polymer is polyvinyl alcohol (PVA). Other Examples include gelatin, polyvinyl pyrolidone (PVP), albumin, and polyethyleneimine (PEI), acacia gum, cellulose derivatives, calcium polypectate, maleic anhydride derivatives, polyacrylic and methacrylic acid, phospholipids, polyglycolide and lactide derivatives, starch, alginates and alginic acid, calcium caseinate, carrageenan, pectins, polyhexametaphosphate, polyvinyl acetate, polyvinyl alcohol, and the like; mixtures thereof; and the like.

In certain embodiments, the composition further comprises one or more surfactants. Exemplary surfactants include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the surfactant is a Tween surfactant (e.g., Tween 60, Tween 80, etc.).

In certain embodiments, the composition further comprises one or more preservatives. Exemplary preservatives may include antioxidants, chelating agents, antimicrobial preservatives, antifungal preservatives, alcohol preservatives, acidic preservatives, and other preservatives.

In certain embodiments, the one or more preservative comprises an antioxidant. Exemplary antioxidants include, but are not limited to, phosphites, dibutyl phosphite, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, sodium sulfite, cysteine hydrochloride, thioglycerol, sodium mercaptoacetate, sodium formaldehyde sulfoxylate (SFS), lecithin, and alpha-tocopherol. In certain embodiments, the antioxidant is dibutyl phosphite or sodium bisulfite ($NaHSO_3$).

In certain embodiments, the one or more preservative comprises a chelating agent. Exemplary chelating agents include, but are not limited to, ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate.

In certain embodiments, the one or more preservative comprises an antimicrobial preservative. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

In certain embodiments, the one or more preservative comprises an antifungal preservative. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid.

In certain embodiments, the one or more preservative comprises an alcohol preservative. Exemplary alcohol preservatives include, but are not limited to, ethanol, polyethylene glycol, phenol, phenolic compounds, bisphenol, chlorobutanol, hydroxybenzoate, and phenylethyl alcohol.

In certain embodiments, the one or more preservative comprises an acidic preservative. Exemplary acidic preservatives include, but are not limited to, vitamin A, vitamin C, vitamin E, beta-carotene, citric acid, acetic acid, dehydroacetic acid, ascorbic acid, sorbic acid, and phytic acid.

Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

In certain embodiments, the composition further comprises one or more diluents. Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

In certain embodiments, the composition further comprises one or more granulating and/or dispersing agents. Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

In certain embodiments, the composition further comprises one or more binding agents. Exemplary binding agents include, but are not limited to, starch (e.g. cornstarch and starch paste); gelatin; sugars (e.g. sucrose, glucose, dextrose, dextrin, molasses, lactose, lactitol, mannitol, etc.); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

In certain embodiments, the composition further comprises one or more buffering agents. Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

In certain embodiments, the composition further comprises one or more lubricating agents. Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

In certain embodiments, the composition further comprises one or more solubilizing or suspending agents. Exemplary solubilizing or suspending agents include, but are not limited to, water, organic solvents, oils, and mixtures thereof. Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof. In certain embodiments, the oil is mineral oil.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

The formulations of the pharmaceutical compositions described herein may be prepared by any method known or hereafter developed in the art of pharmacology. In general, such preparatory methods include the step of bringing the active ingredient (i.e., a glycosylated deltorphin variant) into association with a carrier and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) of the active ingredient.

Preferred dosage forms include oral and parenteral dosage forms. Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Compositions for oral administration are typically liquid or in solid dosage forms. Compositions for oral administration may include protease inhibitors, including organic acids such as citric acid, in order to inhibit pancreatic and brush border proteases. Compositions for oral administration may additionally include absorption enhancers, such as acylcarnitine and lauroylcarnitine, to facilitate the uptake of the peptide through the lumen of the intestine into the systemic circulation by a paracellular transport mechanism. Compositions for oral administration may additionally include detergents to improve the solubility of the peptides and excipients and to decrease interactions with intestinal mucus. Solid form compositions for oral administration, such as tablets or capsules, may typically comprise an enteric coating which further protects the peptides from stomach proteases and permits passage of the tablet or capsule into the small intestine. The solid form composition may additionally comprise a subcoat such as a non-ionic polymer. Examples of preparation of such orally available formulations are disclosed in U.S. Pat. Nos. 5,912,014, 6,086,918 and 6,673,574. The disclosure of each of these documents is hereby incorporated herein by reference.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

The active ingredients can be in micro-encapsulated form with one or more excipients as noted above. The solid dosage forms of tablets, dragees, capsules, pills; and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as may be required. Additionally, the present invention contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the additional ingredients described herein. A pharmaceutical composition of the invention may be prepared, packaged, and/or sold in a formulation suitable for buccal administration. Such formulations may, for example, be in the form of tablets and/or lozenges made using conventional methods, and may, for example, comprise 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* 21$^{st}$ ed., Lippincott Williams & Wilkins, 2005.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Still further encompassed by the invention are kits that comprise one or more inventive complexes and/or compositions. Kits are typically provided in a suitable container (e.g., for example, a glass, foil, plastic, or cardboard package). In certain embodiments, an inventive kit may include one or more pharmaceutical excipients, pharmaceutical additives, therapeutically active agents, and the like, as described herein. In certain embodiments, an inventive kit may include means for proper administration, such as, for example, graduated cups, syringes, needles, cleaning aids, and the like. In certain embodiments, an inventive kit may include instructions for proper administration and/or preparation for proper administration.

The compositions and formulations of the present invention are useful for the treatment of conditions associated with glucose metabolism. Such conditions include, without limitation, the treatment of Syndrome X, diabetes mellitus, hypercholesterolemia, and obesity.

EXAMPLES

Reagents HPLC grade acetonitrile is obtained from Rathburn (Walkersburn, Scotland). Sequencing grade trifluoroacetic acid (TFA), dipeptidyl peptidase IV (DPP IV), isobutylmethylxanthine (IBMX), adenosine 3',5'-cyclic monophosphate (cAMP) adenosine 5'-triphosphate (ATP), and diprotin A (DPA) were purchased from Sigma (Poole, Dorset, UK). RPMI 1640 culture medium, foetal bovine serum, penicillin, and streptomycin are all purchased from Gibco Life Technologies (Paisley, Strathclyde, UK). Fmoc-protected amino acids are purchased from Calbiochem Novabiochem (Beeston, Nottingham, UK). Chromatography columns used in the assay of cAMP, Dowex AG 50 WX, and neutral alumina AG7 are obtained from Bio-Rad (Life Science Research, Alpha Analytical, Larne, Northern Ireland). Tritiated adenine is obtained from Amersham-Pharmacia Biotech, Buckinghamshire, UK. All water used in experiments is purified using a Milli-Q Water Purification System (Millipore, Milford, Mass., USA). All other chemicals used are of analytical grade. [Green et al., Biol. Chem. (2003) 384:1543-51]

Preparation and Purification of GLP-1 and GIP Peptides. GLP-1 and GLP-1 glycopeptides are synthesized on an Applied Biosystems automated peptide synthesizer (model 432 A, Applied Biosystems, Foster City, Calif., USA) using standard solid-phase N-(9-fluorenyl)methy carbonyl (Fmoc) protocols. Glycans may be attached to the peptide through any known means, whether enzymatic or synthetic, including means described in U.S. Pat. Nos. 5,470,949 and 5,767,254, the disclosure of which are hereby incorporated by reference. In the synthesis of GLP-1 peptides, a rink amide MBHA resin is used. Synthetic peptides are cleaved from the resin and purified by reversed-phase HPLC on a Waters Millenium 2010 chromatography system (Software version 2.1.5).

Confirmation of Peptide Identities Using Electrospray Ionization Mass Spectrometry. Intact peptides and degradation fragments are dissolved in 0.12% (v/v) TFA/water and directly injected onto the electrospray ionization source of an LCQ ion-trap mass spectrometer (Finnigan MAT, Hemel Hempstead, Hertfordshire, UK). Spectra are obtained from a quadrupole ion-trap mass analyzer with the detector set to a mass-to charge range m/z of 150-2000. The molecular masses of GLP-1 glycopeptides are calculated from the prominent multiple charged ions using the equation, $M_r=iMi-iM_h$ (where $M_r$ is the molecular mass, Mi is the m/z ratio, i is the number of charges, and $M_h$ is the mass of a proton). [Green et al., Biol. Chem. (2003) 384:1543-51].

Assessment of Peptide Stability to DPP IV in Pooled Human Plasma. GLP-1 glycopeptides (final peptide concentration 2 mM) are incubated with pooled human plasma (7.5 µl) or DPP IV (1.25 mU) for 0 h (control) and 12 h (500 µl; 37° C.; 50 mM triethanolamine-HCl buffer; pH 7.8). Following reaction termination (addition of TFA/H$_2$O 15 ml, 10% (v/v)), the reaction products are applied to a Vydac C-18 analytical column (4.6×250 mm) and the major degradation fragment GLP-1(9-36) amide is separated from intact GLP-1. The column is equilibrated with TFA/H$_2$O (0.12% (v/v)) at a flow rate of 1.0 ml/min. Using 0.1% (v/v) TFA in 70% acetonitrile/H$_2$O, the concentration of acetonitrile in the eluting solvent is raised from 0 to 28% over 10 min, and from 28 to 42% over 30 min. The absorbance is monitored at 206 nm using a SpectraSystem UV 2000 detector (Thermoquest Limited, Manchester, UK) and peaks are collected manually prior to ESI-MS analysis [Green, et al., Id].

Culture of BRIN-BD11 Cells. BRIN-BD11 cells are cultured in RPMI-1640 tissue culture medium containing 10% (v/v) foetal calf serum, 1% (v/v) antibiotics (100 U/ml penicillin, 0.1 mg/ml streptomycin), and 11.1 mM glucose. BRIN-BD 11 cells are produced by electrofusion of an New England Deaconess Hospital (NEDH) rat pancreatic β-cell with RINm5F cell to produce and immortal, glucose sensitive cell line which is described in detail elsewhere. McClenaghan et al., Diabetes (1996) 45:1132-40. All cells are maintained in sterile tissue culture flasks (Corning Glass Works, Sunderland, UK) at 37° C. in an atmosphere of 5% $CO_2$ and 95% air using a LEEC incubator (Laboratory Technical Engineering, Nottingham, UK). [Green et al., Id]

Stimulation of Adenylate Cyclase. BRIN-BD 11 cells are seeded into 24-well plates ($3 \times 10^5$/well) and cultured for 48 h before being pre-incubated in media supplemented with tritiated adenine (2 $mC_i$) for 16 h. The cells are washed twice with cold Hanks' buffered saline (HBS) and test solution (400 µl; 37° C.) is added. The cells are then exposed to varying concentrations ($10^{-10}$-$10^{-5}$ M) of GLP-1 glycopeptides in HBS buffer, in the presence of 1 mM IBMX and 5.6 mM glucose (20 min; 37° C.). Following incubation, test solutions are removed and 300 µl of lysis solution (5% TFA, 3% SDS, 5 mM of unlabelled ATP, and 300 µM of unlabelled cAMP) is added. Dowex and alumina exchange resins are used to separate tritiated cAMP from tritiated adenine and ATP in the cell lysate, as described previously. [Miguel et al., Biochem Pharm. (2003) 65:283-92]. The highest concentration of GLP-1 ($10^{-5}$ M) is used as a maximum. Each peptide is tested by single experiment (n=3) which incorporated an internal control incubation of GLP-1 (60 nM) to ensure consistency and accuracy. [Green et al., Id.]

Insulin Secretory Responses in the Pancreatic β-Cell. BRIN-BD11 cells are seeded into 24-multiwell plates at a density of $1 \times 10^5$/well, and allowed to attach during overnight culture. Acute studies of insulin release are preceded by 40 min pre-incubation at 37° C. in 1.0 ml Krebs-Ringer bicarbonate buffer (115 mM NaCl, 4.7 mM KCl, 1.28 mM $CaCl_2.2H_2O$, 1.2 mM $KH_2PO_4$, 1.2 mM $MgSO_4.7H_2O$, 10 mM $NaHCO_3$, and 5 g/L bovine serum albumin, pH 7.4) supplemented with 1.1 mM glucose. Test incubations are performed at 37° C. in the presence of 5.6 mM glucose with a range of concentrations of GLP-1 glycopeptides ($10^{-12}$-$10^{-6}$ M). After 20 mM incubation, the buffer is removed from each well and aliquots are stored at −20° C. for measurement of insulin. [Green et al., Id.]

Glucose-Lowering and Insulin Secretory Activity in Obese Diabetic (ob/ob) Mice. The in vivo biological activity of GLP-1 glycopeptides is assessed in 12-16 week old obese diabetic (ob/ob) mice. The animals are housed individually in an air-conditioned room at 22±2° C. with a 12 h light:12 h dark cycle. Animals are allowed drinking water ad libitum and continuous access to standard rodent maintenance diet (Trouw Nutrition, Cheshire, UK). Mice are fasted for 18 h and intraperitoneally administered 8 ml/kg body weight with saline (9 g/L NaCl), glucose alone (18 mM/kg body weight), or in combination with GLP-1 or a GLP-1 glycopeptide (25 nM/kg body weight). Blood samples are collected into chilled fluoride/heparin microcentrifuge tubes (Sarstedt, Numbrecht, Germany) immediately prior to injection and at 15, 30, and 60 min post injection, and the plasma obtained is stored at −20° C. All animal studies are carried out in accord with the UK Animals (Scientific Procedures) Act 1986. [Green et al., Id]

Analyses and Statistics. Plasma glucose levels are determined using an Analox glucose analyser (Hammersmith, London, UK), which employs the glucose oxidase method. Insulin levels are assayed by dextran-coated charcoal radioimmunoassay. Incremental areas under plasma glucose and insulin curves (AUC) are calculated using GraphPad PRISM version 3.0 (Graphpad Software, San Diego, Calif., USA), which employs the trapezoidal rule. Results are expressed as means±SEM and data are compared as appropriate using Student's t test, repeated measures ANOVA or one-way ANOVA, followed by the Student-Newman-Keuls post hoc test. Groups of data are considered significantly different if $P<0.05$.

Measurement of Binding Affinity and cAMP Production. Binding affinity is assessed by measuring the inhibition of radiolabeled GLP-1 binding to human GLP-1 receptor-expressing chinese hamster ovary (CHO) cell membrane. Cell membrane fractions (5 µg) are incubated with 62 pM [125I] GLP-1 and GLP-1 analogue (final conc. 10-11 to 10-6 M) in 25 mM HEPES (pH 7.4) containing 5 mM MgCl, 1 mM CaCl2, 0.25 mg/mL bacitracin, and 0.1% bovine serum albumin (BSA) at room temperature for 2 h (100 µL). Membranes are filtered onto a 96-well GF/C plate (PerkinElmer, Inc.) that had been presoaked in 1% polyethylenimine containing 0.5% BSA, and then washed with 25 mM HEPES buffer containing 0.5% BSA (pH 7.4). Radioactivity associated with the lysates is determined using a gamma counter. Nonspecific binding is determined by the amount of binding in the presence of 1 µM unlabeled GLP-1. Dose-response curves are plotted for the individual compounds. IC50 values are calculated using XLfit software (IDBS Inc.). For measurement of cAMP production, human GLP-1 receptor expressing CHO cells are passaged into multiwell plates (4000 cells/well) and cultured for an additional 48 h. The cells are washed with assay buffer (Hanks balanced salt solution containing 20 mM HEPES, 0.1% BSA, pH 7.4) and then exposed to GLP-1 analogues (final conc. 10-12 to 10-6 M) in assay buffer containing 0.33 mM isobutylmethylxanthine and 0.67 mM RO20-1724 at room temperature for 1 h. The cells are lysed with 1% Triton X-100, and the cAMP formed is measured using a cAMP femtomolar kit (Cis Bio international). Dose-response curves are plotted for the individual compounds. EC50 values are calculated using XLfit software. [Ueda et al., J. ACS, 2009 131:6237-45]

Characterization of Stability Against Recombinant Human DPP-IV. GLP-1 or GLP-1 glycopeptide (20-500 µM) is incubated at 37° C. in 100 mM HEPES buffer containing 0.05% Tween80 and 1 mM EDTA-2Na (pH 7.5) with 0.33 µg/mL, 0.66 µg/mL (19), or 1.32 µg/mL recombinant human DPP-IV (60 µL). At 5 or 10 min intervals, 7 µL is removed from the reaction mixture, and the reaction is terminated by the addition of 28 µL of 8 M GuHCl solution. The reaction products are subjected to RP-HPLC on a Develosil RPAQUEOUS—AR-3 2.0°—100 mm at 30° C., and the C-terminal degradation product is quantified by using UV absorption at 210 nm. The initial rate of the degradation reaction is determined from the slope of the linear part obtained by plotting product concentration versus time. The resulting initial rates are plotted versus peptide concentration, and kinetic parameters (KM and KM/kcat) are determined using XLfit software based on the Michaelis-Menten kinetic equation. [Ueda et al., Id.]

Characterization of Stability against Recombinant Human NEP 24.11. The 125 µM GLP-1 or GLP-1 glycopeptide is incubated at 37° C. in 50 mM HEPES buffer containing 50 mM NaCl, and 0.05% Tween 80 with 4 µg/mL recombinant human NEP 24.11 (pH 7.4, 84 µL). After 0.5, 1, 2, 3.5, and 5 h, 8 µL is removed from the reaction mixture, and the reaction is terminated by addition of 32 µL of 8 M GuHCl solution. The reaction products are subjected to RP-HPLC on a Develosil ODSHG—54.6°—150 mm at 30° C., and the area of intact GLP-1 glycopeptide is measured using UV absorption at 210 nm. [Ueda et al., Id.]

Blood Glucose-Lowering Activity in Obese Diabetic db/db Mice. Male BKS.Cg-+ Leprdb/+ Leprdb mice (13-15 weeks of age) are allowed ad libitum access to food and water until the start of the experiment. At t)-2 h, access to food is restricted, and the tip of the tail is cut. At t) 0 min, a 1 µL blood sample is collected. Immediately thereafter, each mouse is injected subcutaneously with test sample (100 nmol/kg) or vehicle, and additional blood samples are collected. The vehicle is saline containing 1% BSA. Blood glucose levels are measured with a glucose oxidase biosensor (DIAMETERR; Arkray, Inc.). The effects of the test samples on blood glucose are expressed as % change relative to the respective pretreatment (t) 0 min) level. The number of mice tested is 6-7 for each group. Data are presented as means (SEM. Statistical differences are analyzed using the Dunnett's multiple comparison test, and P values less than 0.05 are regarded as significant. [Ueda et al., Id.]

While the present invention has been has been described with respect to specific embodiments thereof, it will be evident to those skilled in the art that various modifications and changes may be made thereto without departing from the essential spirit and scope of the invention. Accordingly, the compositions and methods comprising such modifications and changes constitute part of the present invention.

All publications that are referenced within the present specification are hereby incorporated herein by reference for the disclosure and teachings provided in such publications.

The invention claimed is:

1. A GLP-1 agonist comprising a polypeptide having a C-terminal amino acid with an O-linked carbohydrate, the polypeptide sequence selected from the group consisting of: Sequence ID No. 29, Sequence ID No. 30, Sequence ID No. 31, and Sequence ID No. 32, wherein the O-linked carbohydrate is a monosaccharide selected from the group consisting of glucose; galactose; xylose; fructose; mannose; fucose; ribose; deoxyribose; arabinose; and rhamnose.

2. The GLP-1 agonist of claim 1, wherein the monosaccharide is beta-D-glucose.

* * * * *